United States Patent [19]

Rajamani et al.

[11] Patent Number: 5,650,623
[45] Date of Patent: Jul. 22, 1997

[54] PERIMETER SENSING DEVICE

[75] Inventors: Ravi Rajamani, Schenectady; Frederic Ghislain Pla, Clifton Park, both of N.Y.

[73] Assignee: General Electric Company, Schenectady, N.Y.

[21] Appl. No.: 566,744

[22] Filed: Dec. 4, 1995

[51] Int. Cl.$^6$ .................................................. G01T 1/166
[52] U.S. Cl. .............................. 250/336.1; 340/562
[58] Field of Search .............. 250/336.1, 363.05, 250/363.08, 491.1; 340/562, 561

[56] References Cited

U.S. PATENT DOCUMENTS

| | | | |
|---|---|---|---|
| 4,007,418 | 2/1977 | Hanna | 324/72 |
| 4,320,765 | 3/1982 | Alchanka et al. | 340/562 |
| 4,785,743 | 11/1988 | Dolphin | 109/40 |
| 4,796,013 | 1/1989 | Yasuda et al. | 340/562 |
| 5,019,804 | 5/1991 | Fraden | 340/562 |
| 5,486,700 | 1/1996 | Silberklant et al. | 250/363.02 |

*Primary Examiner*—David P. Porta
*Assistant Examiner*—Richard Hanig
*Attorney, Agent, or Firm*—Donald S. Ingraham

[57] ABSTRACT

A perimeter monitoring device is disposed so as to detect passage of objects through a monitored space above a perimeter line and to generate a perimeter signal in correspondence with such a detected passage. The monitoring device includes at least one sensor element disposed along the perimeter line to be monitored and a processing unit coupled to the sensor element so as to detect electrical current generated in the sensor element from the movement of the intruding object past the sensor element. Each sensor element comprises a loop of electrically conductive material that is electrically isolated from the other sensor element, and each of which is separately electrically coupled to the processing unit. The perimeter detection system further comprises an electrical insulation material, such as a mat, that is disposed between the conductive sensor element and the monitored space. The signal generated by the processing unit in correspondence with the detection of an object passing through the monitored area is typically coupled to control mechanisms for the equipment, such as a radiation imager, located within the cordoned area, so that operation of the equipment can be stopped or modified to minimize the chance of the equipment causing harm to an intruder passing across the perimeter line.

6 Claims, 2 Drawing Sheets

PERIMETER SENSING DEVICE

BACKGROUND OF THE INVENTION

This invention relates generally to devices for monitoring the passage of objects across a perimeter line, and in particular to a perimeter monitoring device for use with a radiation imaging system to detect passage of objects across a perimeter line around a cordoned area in which the imaging device is located.

It is necessary to restrict access to the area around certain types of equipment while it is in operation in order to prevent injury or disruption of the operation of the equipment. One example of such type of equipment is radiation imaging equipment, such as is used for medical imaging procedures. Restricting access to the equipment is necessary to prevent physical injury that may result from being struck by movable equipment of the imaging system, such as gantry arms, on which components of the imaging system are mounted.

It is thus desirable to have a perimeter sensing system that can monitor passage of objects (such as people) across a perimeter line surrounding a cordoned area in which the imaging machine is disposed. Such a sensing system is beneficially remote (that is, does not require a human operator in the immediate vicinity) and a system on which the radiation does not have an adverse effect.

SUMMARY OF THE INVENTION

A perimeter monitoring device is disposed so as to detect passage of objects through a monitored space above a perimeter line and to generate a signal in correspondence with such a detected passage. The monitoring device includes at least one sensor element disposed along the perimeter line to be monitored and a processing unit coupled to the sensor element so as to detect electrical current generated in the sensor element from the movement of the intruding object past the sensor element. Each sensor element comprises a loop of electrically conductive material that is electrically isolated from the other sensor element, and each of which is separately electrically coupled to the processing unit. The perimeter detection system further comprises an electrical insulation material, such as a mat, that is disposed between the conductive sensor element and the monitored space. The signal generated by the processing unit in correspondence with the detection of an object passing through the monitored area is typically coupled to control mechanisms for the equipment, such as a radiation imager, located within the cordoned area, so that operation of the equipment can be stopped or modified to minimize the chance of the equipment causing harm to an intruder passing across the perimeter line.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description in conjunction with the accompanying drawings in which like characters represent like parts throughout the drawings, and in which:

The FIG. 1 is a part perspective and part block diagram of a perimeter monitoring device in accordance with this invention disposed.

DETAILED DESCRIPTION OF THE INVENTION

Figure 1:
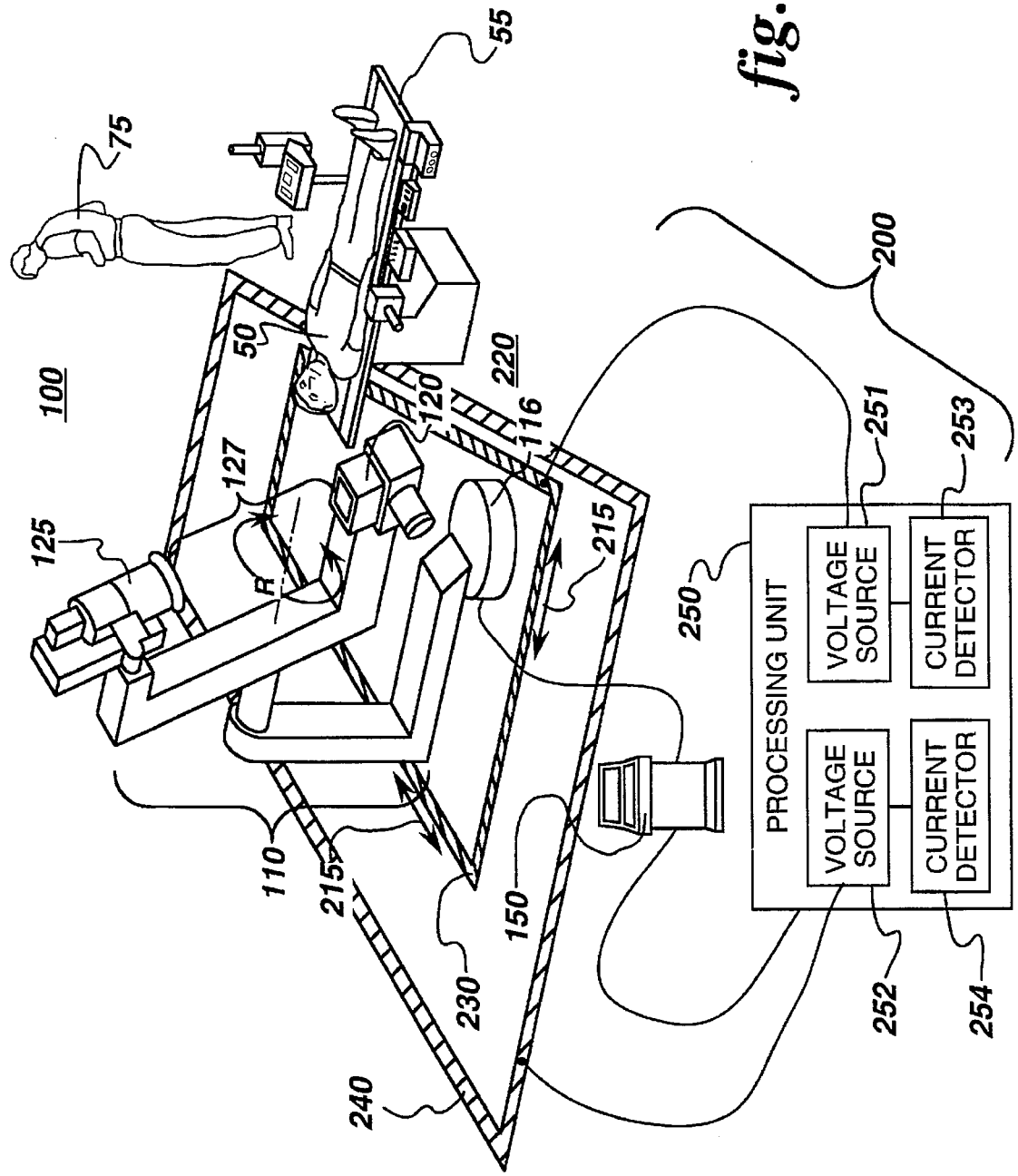

A radiation imaging system 100 comprises a movable gantry assembly 110 that is surrounded by a perimeter monitoring device 200 (FIG. 1). Imaging system 100 is coupled to an imager control system 150 that is used to generate control signals to direct the movement of gantry assembly 110 to effect a desired radiation imaging of a subject 50; perimeter monitoring device 200 is coupled to imager control system 150 to provide a signal to cause cessation or modification of operation of the gantry assembly 110 in the event of certain conditions, such as the detection of the passage of an object, such as an intruding person 75, past a perimeter line 215 that is disposed to define a cordoned area in which gantry assembly 110 is disposed.

Gantry assembly 110 provides a support structure for components of the radiation imaging system. Typically a radiation source 120 (such as an x-ray source or the like) is mounted on one arm and a radiation detector assembly 125, such as an x-ray image-intensifier tube, is attached on another arm so as to be disposed opposite radiation source 120 across an intervening target region 127. Gantry assembly 110 is rotatably mounted on a gantry foundation 116 so that the gantry arms, with the attached imaging components 120, 125, can be rotated around a subject 50, e.g., as indicated by the arrows "R" in FIG. 1.

By way of example and not limitation, radiation imaging system 100 as presented herein is adapted for medical imaging of a patient's body; alternatively, the imaging system of this invention can be used with industrial processes for quality control and the like. Typically the object of study, or subject 50, is a portion of a patient's body, such as the patient's head, that is resting on an examining table 55; the gantry assembly arms move about subject 50 to position radiation source 120 and radiation detector 125 in positions to obtain desired imaging data regarding subject 50. Gantry assembly 110 and movable components thereon are typically driven by drive systems (not shown), such as an electrical motor and transmission, that are responsive to signals from control system 150.

In accordance with this invention, perimeter monitoring device 200 is disposed so as to detect passage of intruding object 75 across a monitored space 210 (shown in phantom in FIG. 2) above a perimeter line 215. Perimeter line 215 (FIG. 1) is typically disposed around gantry assembly 110 and table 55 to provide a cordoned area 220, access to which can be monitored with perimeter monitoring device 200. For purposes of illustration and not limitation, perimeter line 215 is shown in FIG. 1 extending completely around gantry assembly 110 and table 55. Perimeter line 215 is typically disposed around cordoned area 220 which has dimensions such that persons outside of the cordoned area would not be struck by moving portions of the gantry assembly or otherwise harmed by the machinery.

In accordance with this invention at least a first sensor element 230 is disposed along perimeter line 215. Sensor element 230 comprises a conductive material, such as metal plate or metal wire that is electrically coupled to a processing unit (or processor) 250. As illustrated in FIG. 1, sensor element 230 comprises an electrically-continuous length of conductive material that is electrically coupled to processor 250. Sensor element 230 may comprise a loop, or alternatively a line segment terminated at ends and that is electrically coupled to processor 250. The size of sensor element 230 is selected in the design process, in conjunction with components of processor 250, to provide a desired sensitivity of detection; typically larger-dimension sensor elements (using materials having the same conductivity) provides increased area of coverage for detection of passage of object 75 over the sensor element. The area of the sensor element determines the volume of monitored space 210 (FIG. 2) above perimeter line 215. The gain of current detector components in processor 250 can also be adjusted to effect a change in the volume of monitored space 210.

In an alternative embodiment, perimeter monitoring system 200 further comprises a second sensor element 240 (FIG. 1) to provide improved sensitivity as described further below. Second sensor element 240 is similar in all respects to first sensor element 230, electrically isolated from first sensor element 230 and is separately electrically coupled to processor 250. For ease of illustration, second sensor element 240 is illustrated in FIG. 1 disposed at a distance from first sensor element 230; the physical separation between first and second sensor elements 230, 240 is selected in the design process and is typically as small as possible (e.g., within less than an inch to overlapping) so that the respective signals derived from each sensor element each represent the passage of the same intruding object 75.

Each sensor element 230, 240 is respectively electrically coupled to processor 250 to enable electrical signals corresponding to the passage of intruding object 75 past sensor elements 230, 240 to be processed. Processor 250 comprises a first voltage source 251 that is coupled to first sensor element 230 and a first current detector 253 that is coupled to first sensor element 230 so as to detect an induced current flow therein caused by the passage of a body (e.g., intruding object 75) that is at a different electrical potential over a portion of the conductive segment comprising first sensor element 230. By way of example and not limitation, first voltage source comprises means of providing a known DC potential on the sensor element, such as an AC or DC voltage generator (e.g. a battery, DC line voltage, or an AC source rectified to DC, or the like). Voltage source 251 is thus adapted to maintain first sensor element at a given electrical potential, such as at a positive or negative potential with respect to ground. Alternatively, voltage source 251 is adapted to maintain the sensor element to which it is attached at ground potential, in which case source 251 may comprise an appropriate electrical connection to ground. Current detector 253 typically comprises a charge amplifier or high impedance amplifier or the like that is adapted to detect current flow in the sensor element that correspond to the passage of object 75 past first sensor element 230 in monitored space 210.

Most human bodies are at some potential with respect to ground when the person is moving about (e.g., not in physical contact with equipment or material in the room attached to the building or foundation) and wearing footwear that is not electrically conductive (which includes most commonly used footwear materials). Passage of object 75 over a portion of first sensor element 230 results in an induced current in first sensor element 230 when the electrical potential of object 75 is not the same as the electrical potential at which first sensor element 230 is maintained. The induced current caused by passage of object 75 through the monitored space is sensed by current detector 253 and amplified in processor 250 to generate a perimeter signal that corresponds to the detected breach of the perimeter line 215.

In the alternative embodiment of the present invention having second sensor element 240, processor 250 further comprises a second voltage source 252 and a second current detector 254. Second voltage source 252 and second current detector 254 are electrically coupled to second sensor element 240 and are otherwise similar in all respects to first voltage source 251 and first current detector 252 as described above except that second voltage source 252 is adapted to maintain second sensor element 240 at an electrical potential different from the electrical potential of first sensor element 230. For example, typically one of the two sensor elements is maintained at ground potential and the second of the two sensor elements is maintained at a voltage potential other than ground (typically, up to about 5 volts with respect to ground). In this manner, regardless of the potential of intruding object 75, a voltage difference will exist between the object and at least one (and possibly both) of the sensor elements and thus perimeter monitoring system is able to detect the passage of intruding object 75 as discussed above.

Processing unit 250 is further coupled to imaging system controller 150 so as to provide a perimeter signal thereto corresponding to the induced current in at least one sensor element that is indicative of an object within monitored space 210. Imaging system controller 150 is adapted to process the perimeter signal such that, based on predetermined parameters, e.g., a voltage output of the current detector above a predetermined noise level (which noise level would be determined in calibration tests for a given installation of the perimeter monitoring device). Controller 150 generates a control signal to cease or modify operations of imaging system 100, such as stopping irradiation of subject 50 and stopping motion of gantry assembly 110. Operation of radiation imaging system 1 00 is typically only resumed after an operator has ascertained that any intruding object 75 is removed from cordoned area 220.

Figure 2:
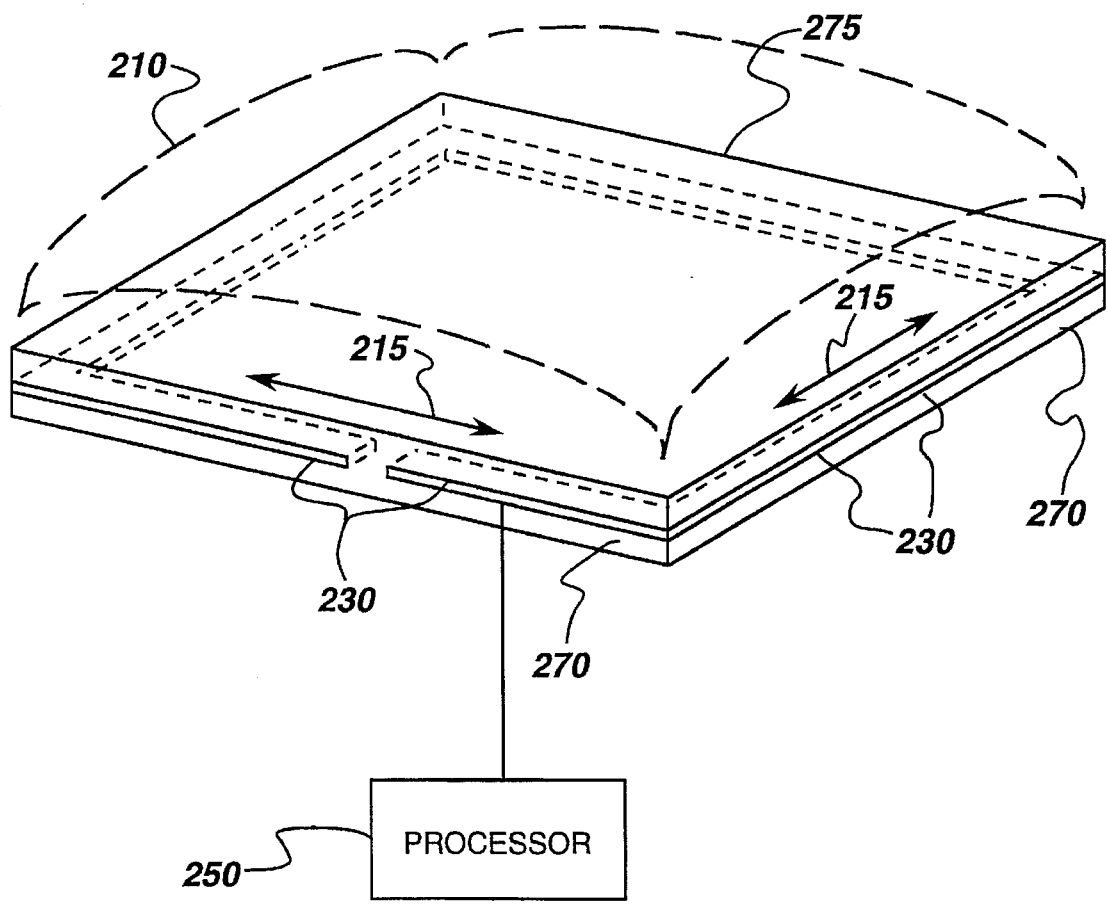
FIG. 2 is a part cross section and part perspective view of a portion of a sensor element in accordance with the present invention.

In accordance with the present invention, each sensor element 230 is disposed such that an electrically insulative material 270 (FIG. 2) is disposed between the sensor element and intruding object 75 (for ease of illustration, only sensor element 230 is shown in FIG. 2; second sensor element 240 is similarly disposed in an electrically insulative material). Each sensor element is further electrically isolated from the other sensor element, and commonly electrically isolated from the platform on which it rests (the only electrical connection being to the respective voltage source in processor 250. Typically insulative material 270 comprises a robust material, an may comprise an organic or inorganic material. Sensor elements 230 are typically disposed in a layer of insulative material 270 to form a mat 275 so as to provide a compact and readily positionable vehicle for positioning sensor element 230 along a desired perimeter line 215. Mat 275 may further comprise second sensor element 240 (not shown); alternatively, first and second sensor elements 230, 240 can be disposed in respective mats. Mat 275 typically has a thickness in the range of between about one-half mm and 5 mm such that it can be placed on a floor around cordoned area 220 without providing an impediment to persons walking onto and over the mat.

It will be apparent to those skilled in the art that, while the invention has been illustrated and described herein in accordance with the patent statutes, modifications and changes may be made in the disclosed embodiments without departing from the true spirit and scope of the invention. It is, therefore, to be understood that the appended claims are intended to cover all such modifications and changes as fall within the true spirit of the invention.

What is claimed is:

1. A perimeter monitoring device for detecting passage of an intruding object within a monitored space above a perimeter line around a cordoned area, the perimeter sensing device comprising:

at least a first and a second electrically conductive sensor element disposed along said perimeter line, each of said sensor elements being electrically insulated from the other; and an electrical charge sensing processing unit coupled respectively to each of said sensor elements so as to detect respective electrical currents generated in each of said sensor elements from the movement of said intruding object past said respective sensor elements within said monitored space;

said processing unit further comprising a respective voltage source coupled to each of said sensor elements, each respective voltage source being maintained at an electrical potential different from the other voltage sources.

2. The perimeter monitoring device of claim 1 further comprising an electrical insulation material disposed between said sensor element and said monitored area above said sensor elements.

3. The perimeter monitoring device of claim 2 wherein said electrical insulation material comprises an insulative mat in which said sensor elements are embedded.

4. The perimeter monitoring device of claim 1 wherein said processor generates a perimeter signal in correspondence with a detected electrical current flow induced by movement of said intruding body though said monitored space, said intruding body having an electrical potential different than the electrical potential of at least one of said sensor elements.

5. A radiation imaging system comprising:

a gantry assembly, said assembly comprising a gantry arm having a radiation imaging system component mounted thereon, said gantry arm being movably coupled to a positioning device so as to dispose said radiation imaging system component in a spaced relationship with respect to a target;

a perimeter monitoring device for detecting passage of an intruding object within a monitored space above a perimeter line disposed around said gantry assembly such that the movable gantry arm is disposed within a cordoned area defined by said perimeter line, said the perimeter sensing device comprising:

at least a first and a second sensor element electrically insulated from one another and disposed along said perimeter line;

an electrical insulation mat disposed between said sensor elements and said monitored area above said sensor elements; and a processing unit respectively coupled to each said sensor elements so as to detect electrical current generated in said sensor element from the movement of an intruding object past respective ones of said sensor element within a monitored space around said respective sensor element;

said processing unit further comprising a respective voltage source coupled to each of said sensor elements, each of said respective sensor element voltage sources being maintained at a different voltage potential.

6. The radiation imaging system of claim 5 wherein said processing unit generates a signal responsive to electrical current in at least one of said sensor elements to control motion of said movable gantry arm.

* * * * *